(12) United States Patent
Desjardin et al.

(10) Patent No.: US 11,583,315 B2
(45) Date of Patent: Feb. 21, 2023

(54) SURGICAL ACCESS DEVICE INCLUDING VARIABLE LENGTH CANNULA

(71) Applicant: Covidien LP, Mansfield, MA (US)

(72) Inventors: Kevin M. Desjardin, Prospect, CT (US); Astley C. Lobo, West Haven, CT (US); Garrett P. Ebersole, Hamden, CT (US); Christopher A. Tokarz, Torrington, CT (US); Douglas M. Pattison, East Hartford, CT (US)

( * ) Notice: Subject to any disclaimer, the term of this patent is extended or adjusted under 35 U.S.C. 154(b) by 121 days.

(21) Appl. No.: 17/092,730

(22) Filed: Nov. 9, 2020

(65) Prior Publication Data

US 2022/0142671 A1 May 12, 2022

(51) Int. Cl.
*A61B 17/34* (2006.01)

(52) U.S. Cl.
CPC .. *A61B 17/3423* (2013.01); *A61B 2017/3443* (2013.01); *A61B 2017/3486* (2013.01)

(58) Field of Classification Search
CPC ............ A61B 17/3423; A61B 17/3417; A61B 2017/3443; A61B 2017/3486; A61B 2017/3433; A61B 2017/00991; A61B 1/32; A61M 29/00
See application file for complete search history.

(56) References Cited

U.S. PATENT DOCUMENTS

| | | | |
|---|---|---|---|
| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari et al. |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

International Search Report and Written Opinion dated Apr. 8, 2022 issued in corresponding PCT Appln. No. PCT/US2021/057667.

*Primary Examiner* — Kevin T Truong
*Assistant Examiner* — Tracy L Kamikawa
(74) *Attorney, Agent, or Firm* — Carter, DeLuca & Farrell LLP

(57) ABSTRACT

A surgical access device includes a cannula having a variable length. The cannula may include a shaft assembly including an outer shaft, an intermediate shaft disposed within and longitudinal slidable relative to the outer shaft, and an inner shaft disposed within and longitudinal slidable relative to the intermediate shaft. The shaft assembly is movable between an unextended position, a fully extended position, and a semi-extended position between the unextended and fully extended positions. The cannula may include a shaft having annular folds formed therein. The annular folds are axially movable relative to each other such that the shaft is longitudinally movable between an unextended position and a plurality of extended positions.

20 Claims, 12 Drawing Sheets

(56) References Cited

U.S. PATENT DOCUMENTS

| | | |
|---|---|---|
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Amey |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,300,448 B2 | 11/2007 | Criscuolo et al. |
| 7,691,089 B2 | 4/2010 | Gresham |
| 7,811,303 B2 * | 10/2010 | Fallin ............... A61B 17/3417 606/191 |
| 8,206,425 B2 * | 6/2012 | Khanna ............... A61B 17/688 606/324 |

(56) References Cited

U.S. PATENT DOCUMENTS

| | | | |
|---|---|---|---|
| 8,425,532 B2 * | 4/2013 | Flom | A61F 2/32 606/104 |
| 8,454,645 B2 | 6/2013 | Criscuolo et al. | |
| 8,926,508 B2 | 1/2015 | Hotter | |
| 10,390,813 B2 * | 8/2019 | Alexander | A61B 1/00165 |
| 2003/0093105 A1 * | 5/2003 | Huffmaster | A61M 25/04 606/192 |
| 2003/0153926 A1 | 8/2003 | Schmieding et al. | |
| 2003/0236505 A1 | 12/2003 | Bonadio et al. | |
| 2004/0138702 A1 * | 7/2004 | Peartree | B25B 5/12 606/213 |
| 2004/0260246 A1 | 12/2004 | Desmond | |
| 2005/0096507 A1 * | 5/2005 | Prosek | A61B 17/34 606/1 |
| 2006/0200185 A1 | 9/2006 | Marchek et al. | |
| 2006/0200186 A1 * | 9/2006 | Marchek | A61B 17/0218 606/191 |
| 2007/0162066 A1 * | 7/2007 | Lyon | A61B 17/3421 606/191 |
| 2008/0228213 A1 | 9/2008 | Blakeney et al. | |
| 2013/0197571 A1 * | 8/2013 | Hariton | A61B 17/0057 606/213 |
| 2018/0271557 A1 * | 9/2018 | Buyda | A61B 17/3421 |
| 2019/0059937 A1 * | 2/2019 | Buyda | A61B 17/3423 |
| 2019/0307937 A1 * | 10/2019 | Fitzgerald | A61B 17/3462 |
| 2020/0337722 A1 * | 10/2020 | Charles | A61B 17/3423 |

FOREIGN PATENT DOCUMENTS

| | | |
|---|---|---|
| EP | 0880939 A1 | 12/1998 |
| EP | 3420985 A2 | 1/2019 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2005072402 A2 | 8/2005 |
| WO | 2016186905 A1 | 11/2016 |
| WO | 2018165367 A1 | 9/2018 |

* cited by examiner

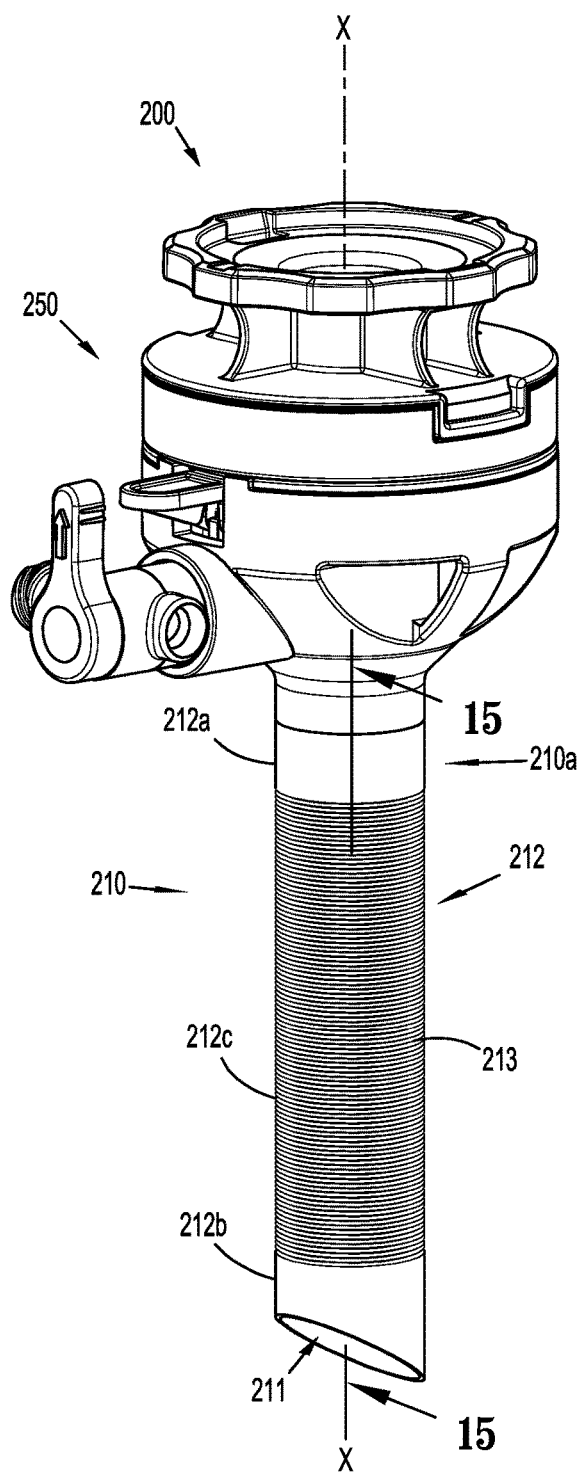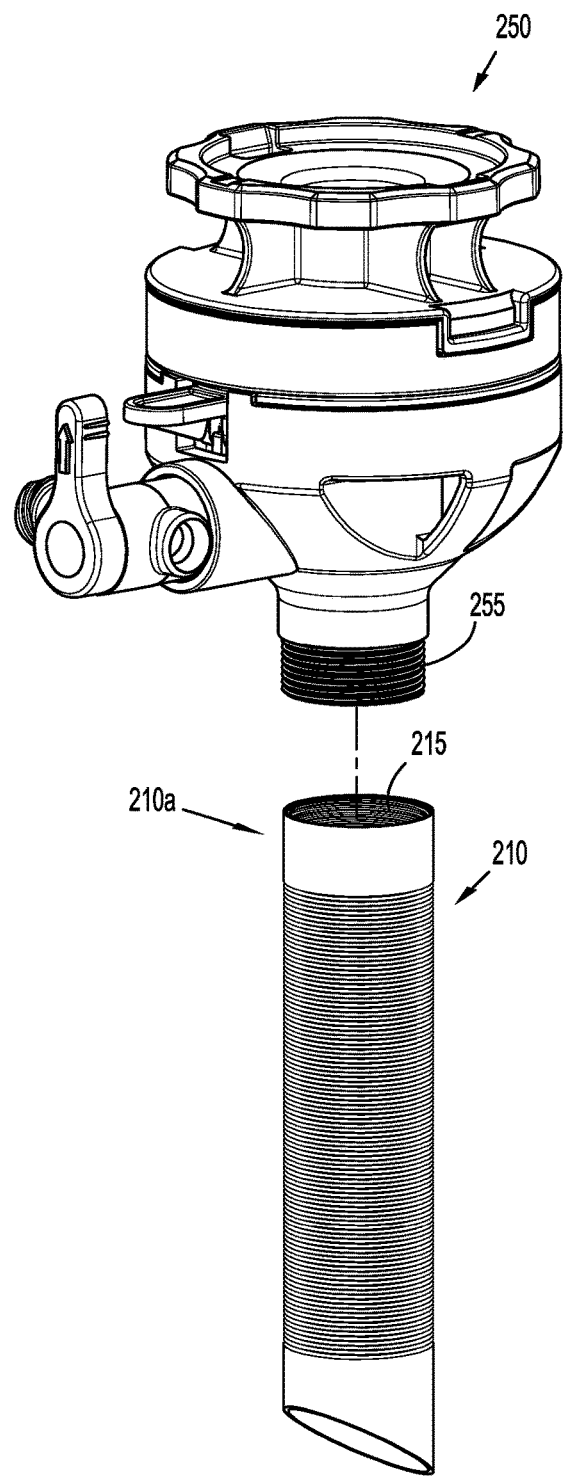
FIG. 13
FIG. 14

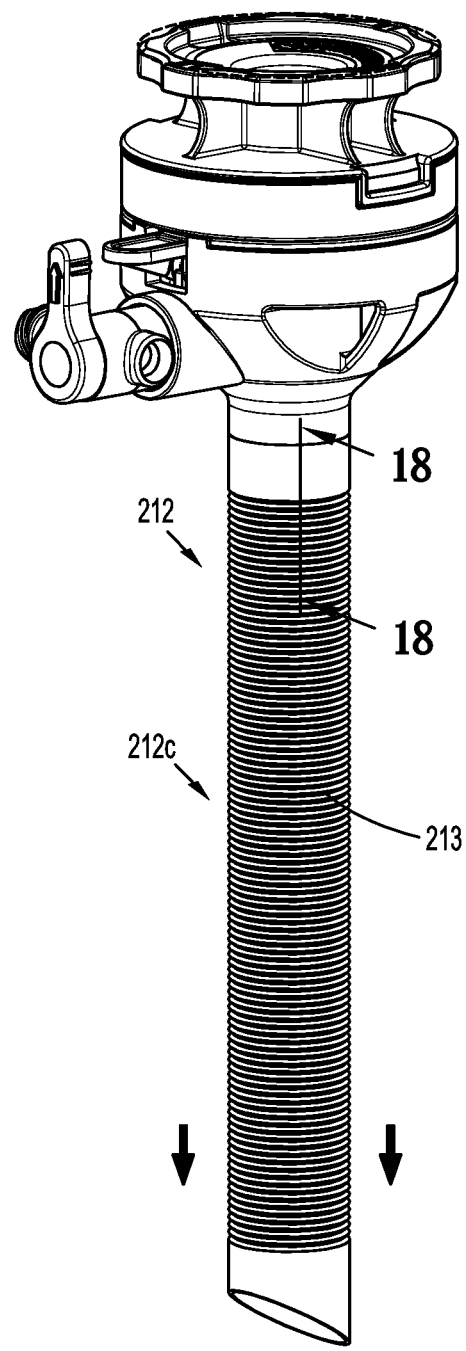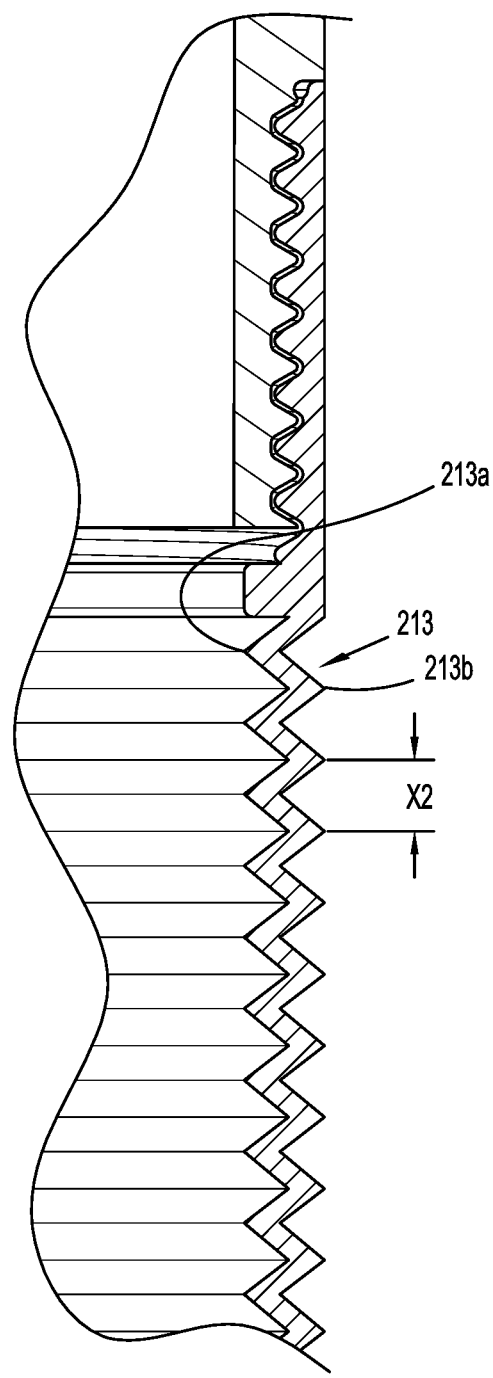
FIG. 17
FIG. 18

SURGICAL ACCESS DEVICE INCLUDING VARIABLE LENGTH CANNULA

FIELD

The present disclosure relates generally to surgical devices. In particular, the present disclosure relates to a surgical access device including a cannula having a variable length to accommodate different tissue wall thicknesses.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an inflatable anchor to prevent the cannula from backing out of the opening in the abdominal wall, for example, during withdrawal of the laparoscopic instrument from the cannula.

Cannulas are available in different lengths and a surgeon chooses a cannula based on the thickness of the abdominal wall of a patient. Factors, such as the patient's height, weight, sex, and overall body composition provide the surgeon with information to help choose a cannula (e.g., short, standard, or long), however, abdominal wall thickness can still vary between patients with similar statistics. This may lead to opening and trying cannulas of different lengths which can add time and cost to a surgical procedure.

SUMMARY

This disclosure generally relates to cannulas that can achieve different lengths to accommodate varying tissue wall thicknesses. The length of the shaft of the cannula is adjustable so that the cannula can be customized to each individual patient. This adjustability allows a surgeon to set the length of the cannula based on patient need. The variable length cannula, as compared to a fixed length cannula, is universal and may reduce the number of types of cannulas needed in a hospital, save a surgeon the difficulty of choosing a cannula having an optimal length for a particular patient, and/or minimize the need to open multiple cannulas if the incorrect length is chosen.

The variable length cannula of the present disclosure may also include fixation mechanisms for securing the cannula within tissue regardless of the chosen shaft length. The cannula may include an inflatable balloon and/or a retention collar to provide fixation on one and/or both sides of a tissue wall (e.g., fixation in one or two directions during instrument removal and/or insertion), and/or may include grips on an outer surface of the shaft that engage the opening in the tissue wall to aid in fixation within the tissue.

In one aspect, the disclosure provides a surgical access device including a cannula having a shaft assembly including an outer shaft, an intermediate shaft disposed within and longitudinal slidable relative to the outer shaft, and an inner shaft disposed within and longitudinal slidable relative to the intermediate shaft. The shaft assembly is movable between an unextended position, a fully extended position, and a semi-extended position between the unextended and fully extended positions.

The inner shaft may be movable within the intermediate shaft between a proximal-most position and a distal-most position and the intermediate shaft may be movable within the outer shaft between a proximal-most position and a distal-most position. When the shaft assembly is in the unextended position, the inner and intermediate shafts may be in the proximal-most positions, when the shaft assembly is in the fully extended position, the inner and intermediate shafts may be in the distal-most positions, and when the shaft assembly is in the semi-extended position, the inner shaft may be in the proximal-most position and the intermediate shaft may be in the distal-most position.

A distal end portion of the outer shaft may include an annular ridge on an inner surface thereof and the intermediate shaft may include proximal and distal annular grooves defined in an outer surface thereof. When the shaft assembly is in the unextended position, the annular ridge of the outer shaft may be engaged with the distal annular groove of the intermediate shaft and when the shaft assembly is in the semi-extended and fully extended positions, the annular ridge of the outer shaft may be engaged with the proximal annular groove of the intermediate shaft.

A distal end portion of the intermediate shaft may include an annular ridge on an inner surface thereof and the inner shaft may include proximal and distal annular grooves defined in an outer surface thereof. When the shaft assembly is in the unextended and semi-extended positions, the annular ridge of the intermediate shaft may be engaged with the distal annular groove of the inner shaft and when the shaft assembly is in the fully extended position, the annular ridge of the intermediate shaft may be engaged with the proximal annular groove of the inner shaft.

A first gasket may be disposed between the intermediate and outer shafts and a second gasket may be disposed between the inner and intermediate shafts.

The surgical access device may further include a balloon operably associated with the cannula. A proximal portion of the balloon may be secured to the outer shaft of the shaft assembly and a distal portion of the balloon may be secured to the inner shaft of the shaft assembly. An inflation channel may be defined in an outer surface of the outer shaft of the shaft assembly and in fluid communication with the balloon. The surgical access device may further include an anchor inflation port coupled to the outer shaft of the shaft assembly and in fluid communication with the inflation channel of the outer shaft.

The surgical access device may further include an instrument housing coupled to the cannula. The instrument housing may be secured to the outer shaft of the shaft assembly of the cannula.

The surgical access device may further include a retention collar movably positioned along the shaft assembly of the cannula.

In another aspect, the disclosure provides a surgical access device including a cannula having a shaft defining an access lumen therethrough. The shaft has annular folds formed therein. The annular folds are axially movable relative to each other such that the shaft is longitudinally movable between an unextended position and a plurality of extended positions.

The annular folds may be formed in a central portion of the shaft. The central portion of the shaft may extend a majority length of the shaft. The shaft may include proximal and distal end portions having fixed lengths.

The annular folds may include alternating inner and outer fold peaks. The outer fold peaks may be spaced a first axial distance relative to each other when the shaft is in the unextended position and a second axial distance relative to each other when in the shaft is in one of the plurality of extended positions. The second axial distance may be greater than the first axial distance. The outer fold peaks may be pointed for tissue fixation.

The surgical access device may further include an instrument housing coupled to the cannula.

The details of one or more aspects of the disclosure are set forth in the accompanying drawings and the description below. Other features, objects, and advantages of the aspects described in this disclosure will be apparent from the description and drawings, and from the claims.

BRIEF DESCRIPTION OF THE DRAWINGS

FIG. 13 is a perspective view of a surgical access device in accordance with another aspect of the present disclosure, shown with a cannula of the surgical access device in an unextended state;

FIG. 14 is a perspective view of the surgical access device of FIG. 13, shown with the cannula separated from an instrument housing of the surgical access device;

FIG. 17 is a perspective view of the surgical access device of FIG. 13, shown with the cannula in an extended state; and FIG. 18 is a cross-sectional view of the surgical access device of FIG. 17, taken along section line 18-18 of FIG. 17.

DETAILED DESCRIPTION

Figure 1:
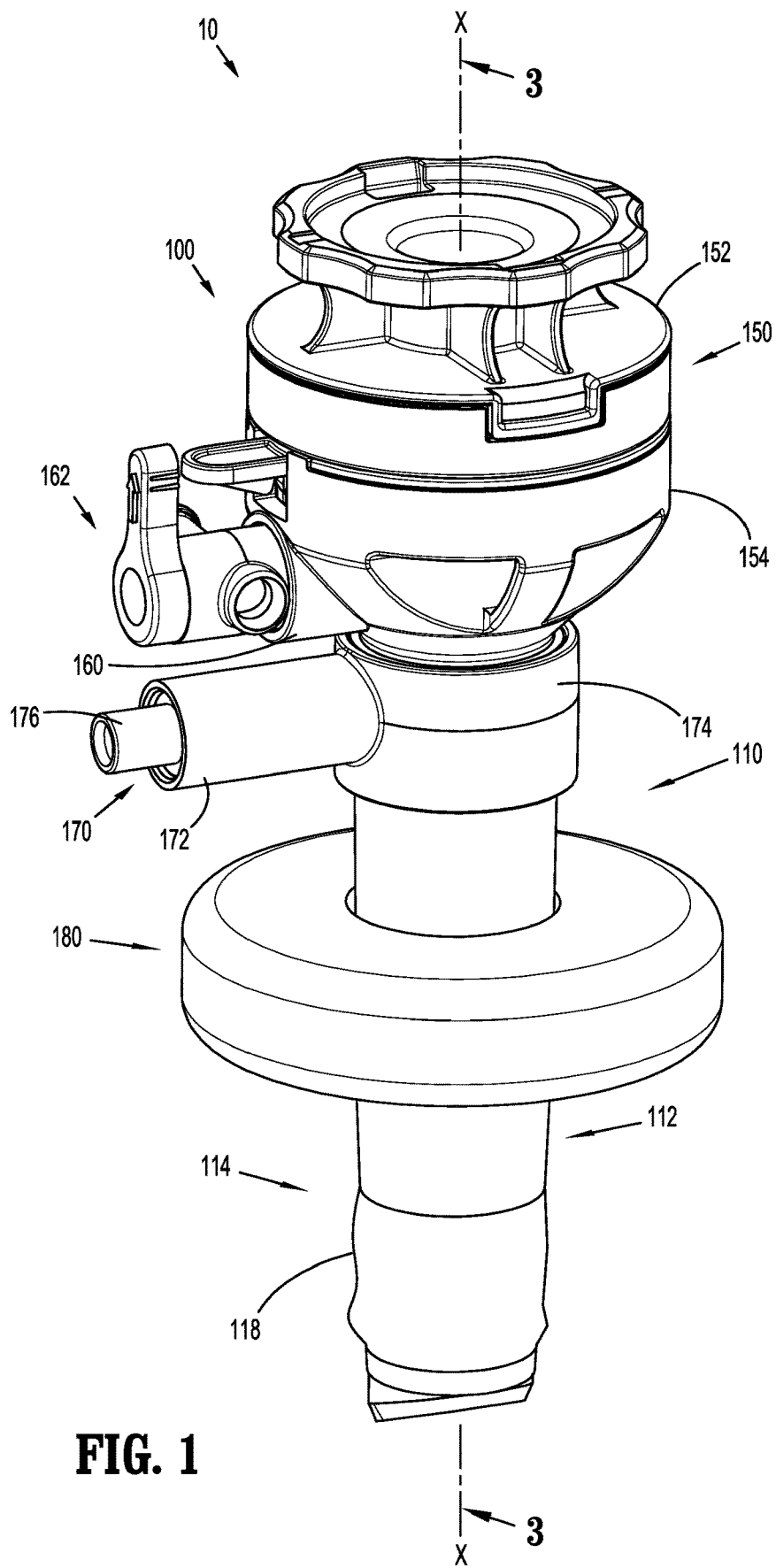
FIG. 1 is a perspective view of a surgical access assembly including a surgical access device in accordance with an aspect of the disclosure, shown with a cannula of the surgical access device in an unextended position.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Surgical access assemblies with obturators, known as trocar assemblies, are employed during minimally invasive surgery, e.g., laparoscopic surgery, and provide for the sealed access of surgical instruments into an insufflated body cavity, such as the abdominal cavity. The surgical access assemblies of the present disclosure include a surgical access device having an instrument housing mounted on a cannula. An obturator (not shown) is insertable through the instrument housing and the cannula. The obturator can have a blunt distal end, or a bladed or non-bladed penetrating distal end, and can be used to incise and/or separate tissue of the abdominal wall so that the surgical access assembly can be introduced into the abdomen. The handle of the obturator can engage or selectively lock into the instrument housing of the surgical access device.

In various aspects, a bladeless optical trocar obturator may be provided that permits separation of tissue planes in a surgical procedure and visualization of body tissue fibers as they are being separated, thereby permitting a controlled traversal across a body wall. In other aspects, the trocar obturator may be bladeless without being optical, e.g., without providing contemporaneous visualization thereof through the distal tip of the trocar obturator. The bladeless trocar obturator may be provided for the blunt dissection of the abdominal lining during a surgical procedure.

Trocar obturators suitable for use with the surgical access devices of the present disclosure are known and include, for example, bladed, bladeless, blunt, optical, and non-optical. For a detailed description of the structure and function of exemplary trocar assemblies, including exemplar trocar obturators, reference may be made to PCT Publication No.

WO 2016/186905, the entire content of which is hereby incorporated by reference herein.

Figure 2:
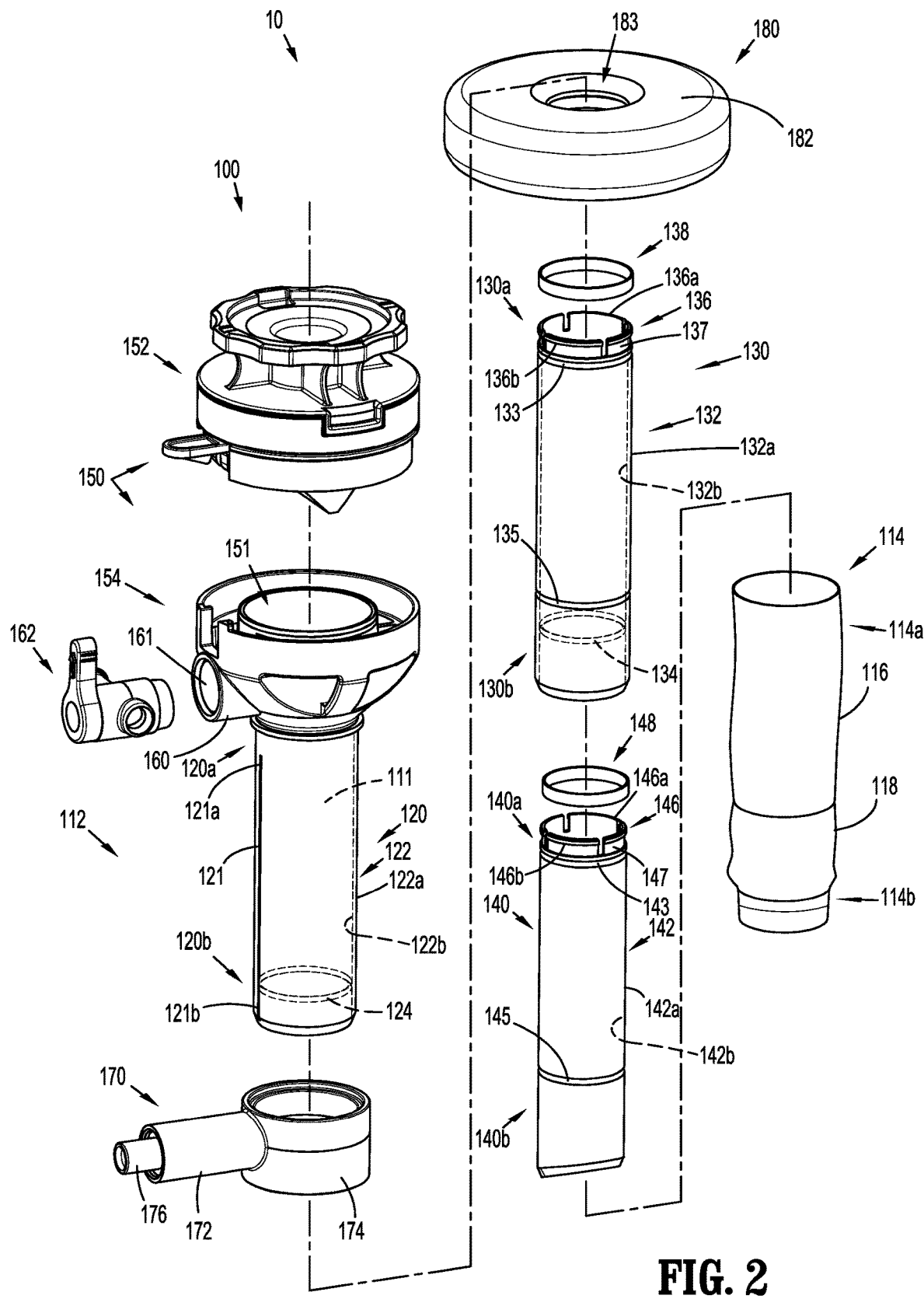
FIG. 2 is an exploded view of the surgical access assembly of FIG. 1.
Figure 3:
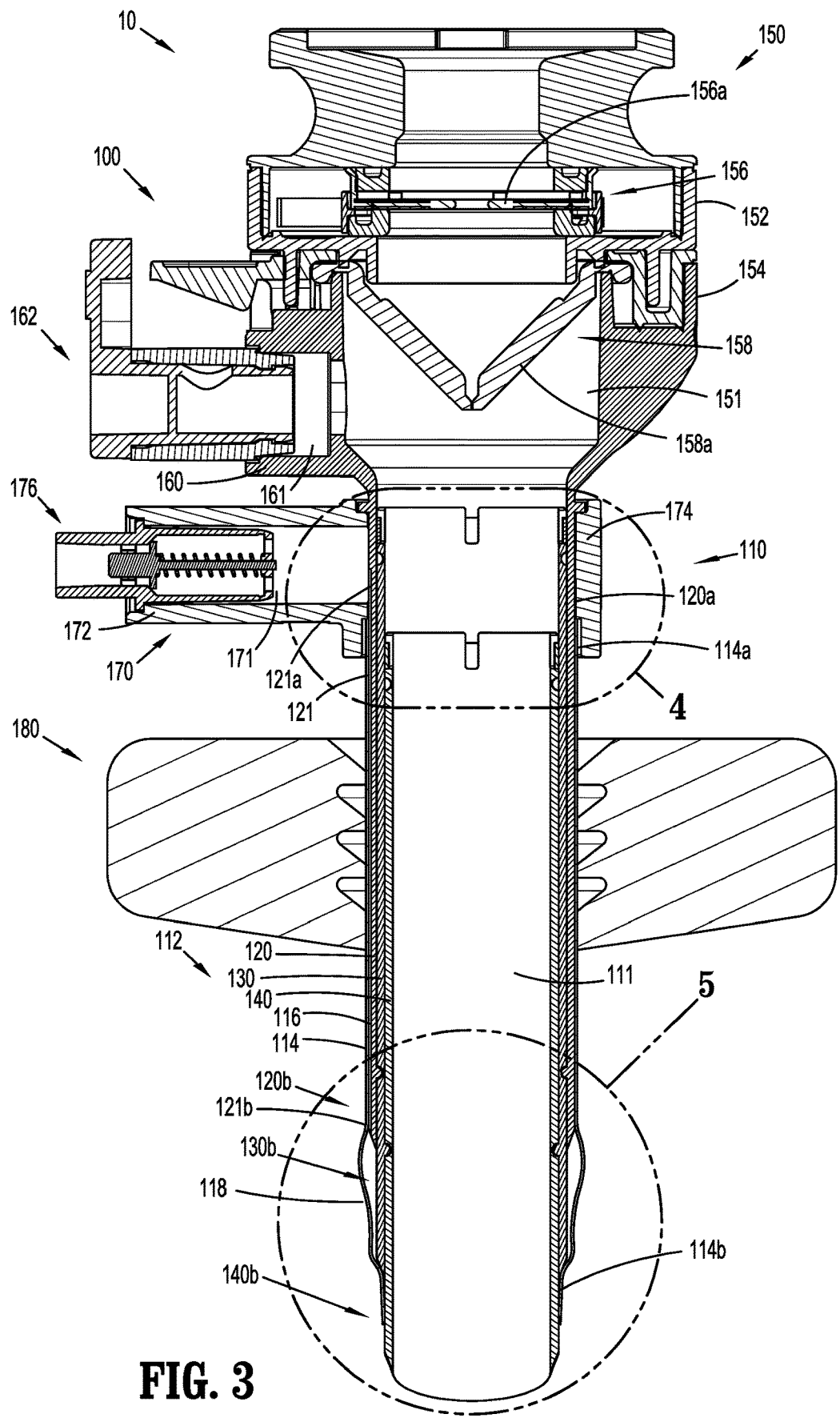
FIG. 3 is cross-sectional view of the surgical access assembly of FIG. 1, taken along section line 3-3 of FIG. 1.

FIGS. 1-3 illustrates a surgical access assembly 10 including a surgical access device 100 and a retention collar 180 supported on the surgical access device 100. The surgical access assembly 10 will further be described to the extent necessary to disclose aspects of the disclosure. For a detailed description of the structure and function of exemplary surgical access assemblies, including exemplar surgical access devices and exemplar retention collars, reference may be made to U.S. Pat. Nos. 7,300,448; 7,691,089; and 8,926,508, the entire content of each of which is hereby incorporated by reference herein. Accordingly, it should be understood that a variety of surgical access assemblies and devices may utilize the variable length cannula of the present disclosure.

The surgical access device 100 includes a cannula 110 and an instrument housing 150 secured to the cannula 110. The cannula 110 generally includes a shaft assembly 112 extending along a longitudinal axis "X" and defining an access lumen 111 for reception and passage of a surgical instrument (not shown) therethrough. The shaft assembly 112 includes an outer shaft or first shaft segment 120, an intermediate shaft or second shaft segment 130, and an inner shaft or third shaft segment 140. The outer, intermediate, and inner shafts 120, 130, 140 are coaxial and telescopically mated so that the shaft assembly 112 is movable between an unextended position (FIG. 6), a semi-extended position (FIG. 7), and a fully extended position (FIG. 10), as described in further detail below.

As seen in FIG. 2, the outer shaft 120 includes an elongated body 122 having a generally cylindrical shape and including an outer surface 122a and an inner surface 122b (shown in phantom). An inflation channel 121 is defined in the outer surface 122a of the elongated body 122 and extends longitudinally along a length thereof. The inflation channel 121 may extend along a majority of the length of the elongated body 122 from a proximal end portion 120a to a distal end portion 120b of the outer shaft 120. The proximal end portion 120a of the outer shaft 120 supports the instrument housing 150 thereon such that the outer shaft 120 is secured to, and longitudinally fixed relative to, the instrument housing 150. The distal end portion 120b of the outer shaft 120 includes an annular ridge 124 (shown in phantom) on the inner surface 122b of the elongated body 122. The annular ridge 124 is raised relative to the inner surface 122b and extends into the access lumen 111. The annular ridge 124 may be in the form of a rib, band, bump, or other protrusion within the purview of those skilled in the art. In some aspects, the annular ridge 124 is integrally formed within the outer shaft 120 and, in some other aspects, the annular ridge 124 is a separate component, such as a rubber gasket or other mechanical interface that is secured (e.g., overmolded) to the outer shaft 120.

The intermediate shaft 130 includes an elongated body 132 having a generally cylindrical shape and including an outer surface 132a and an inner surface 132b (shown in phantom). The outer surface 132a of the elongated body 132 is sized to closely fit the inner surface 122b of the outer shaft 120 and is configured to be slidably disposed therein. A proximal end portion 130a of the intermediate shaft 130 includes a proximally extending collar 136 defining an annular recess 137 in an outer surface thereof. The annular recess 137 is configured to receive a gasket 138 therein for sealing engagement between the intermediate shaft 130 and the outer shaft 120. The collar 136 may have first and second collar sections 136a, 136b that allow the collar 136 to flex, which, together with the gasket 138, maintains a fluid tight seal between the intermediate shaft 130 and the outer shaft 120 while allowing a little give during movement of the intermediate shaft 130 relative to the outer shaft 120. A proximal annular groove 133 is defined in the outer surface 132a of the elongated body 132 distal to the collar 136 in the proximal end portion 130a of the intermediate shaft 130 and a distal annular groove 135 is defined in the outer surface 132a of the elongated body 132 in the distal end portion 130b of the intermediate shaft 130. The proximal and distal annular grooves 133, 135 are sized and shaped to receive the annular ridge 124 of the outer shaft 120 therein to limit travel of the intermediate shaft 130 relative to the outer shaft 120. In some aspects, the annular ridge 124 achieves a seal between the outer shaft 120 and the intermediate shaft 130 when the annular ridge 124 is engaged with the proximal or distal annular groove 133, 135. The distal end portion 130b of the intermediate shaft 130 also includes an annular ridge 134 (shown in phantom) on the inner surface 132b of the elongated body 132.

The inner shaft 140 includes an elongated body 142 having a generally cylindrical shape and including an outer surface 142a and an inner surface 142b (shown in phantom). The elongated body 142 is sized to closely fit the inner surface 132b of the elongated body 132 of the intermediate shaft 130 and is configured to be slidably disposed therein. A proximal end portion 140a of the inner shaft 140 includes a proximally extending collar 146 defining an annular recess 147 in an outer surface thereof. The annular recess 147 is configured to receive a gasket 148 therein for sealing engagement between the inner shaft 140 and the intermediate shaft 130. The collar 146 may have first and second collar sections 146a, 146b that allow the collar 146 to flex, which, together with the gasket 148, maintains a fluid tight seal between the inner shaft 140 and the intermediate shaft 130 while allowing a little give during movement of the inner shaft 140 relative to the intermediate shaft 130. A proximal annular groove 143 is defined in the outer surface 142a of the elongated body 142 distal to the collar 146 in the proximal end portion 140a of the inner shaft 140 and a distal annular groove 145 is defined in the outer surface 142a of the elongated body 142 in the distal end portion 140b of the inner shaft 140. The proximal and distal annular grooves 143, 145 are sized and shaped to receive the annular ridge 134 of the intermediate shaft 130 therein to limit travel of the inner shaft 140 relative to the intermediate shaft 130. In some aspects, the annular ridge 134 achieves a seal between the intermediate shaft 130 and the inner shaft 140 when the annular ridge 134 is engaged with the proximal or distal annular groove 143, 145.

As seen in FIGS. 2 and 3, the cannula 110 further includes a balloon 114 operably associated with the shaft assembly 112. The balloon 114 includes a sleeve 116 and an expandable anchor 118. The expandable anchor 118 secures the cannula 110 against an inner surface of a body wall (see e.g., FIG. 6). The balloon 114 is positioned around the shaft assembly 112 with a proximal portion 114a of the balloon 114 secured to the proximal end portion 120a of the outer shaft 120 and a distal portion 114b of the balloon 114 secured to the distal end portion 140b of the inner shaft 140. The proximal portion 114a of the balloon 114 is secured to the outer shaft 120 at a location distal to a proximal end portion 121a of the inflation channel 121 and the distal portion 114b of the balloon 114 is secured to the inner shaft 140 at a location distal to the distal annular groove 145. The balloon 114 is secured to the outer and inner shafts 120, 140 (e.g., by adhesives and/or welding) to create hermetic contact therebetween. The sleeve 116 is positioned distal to the proximal end portion 121a of the inflation channel 121 defined in the outer shaft 120 of the shaft assembly 112 so that the inflation channel 121 is open to fluid communication with a fluid source (not shown) and the expandable anchor 118 is positioned distal to a distal end portion 121b of the inflation channel 121 so that the expandable anchor 118 is in fluid communication with the inflation channel 121.

Figure 10:
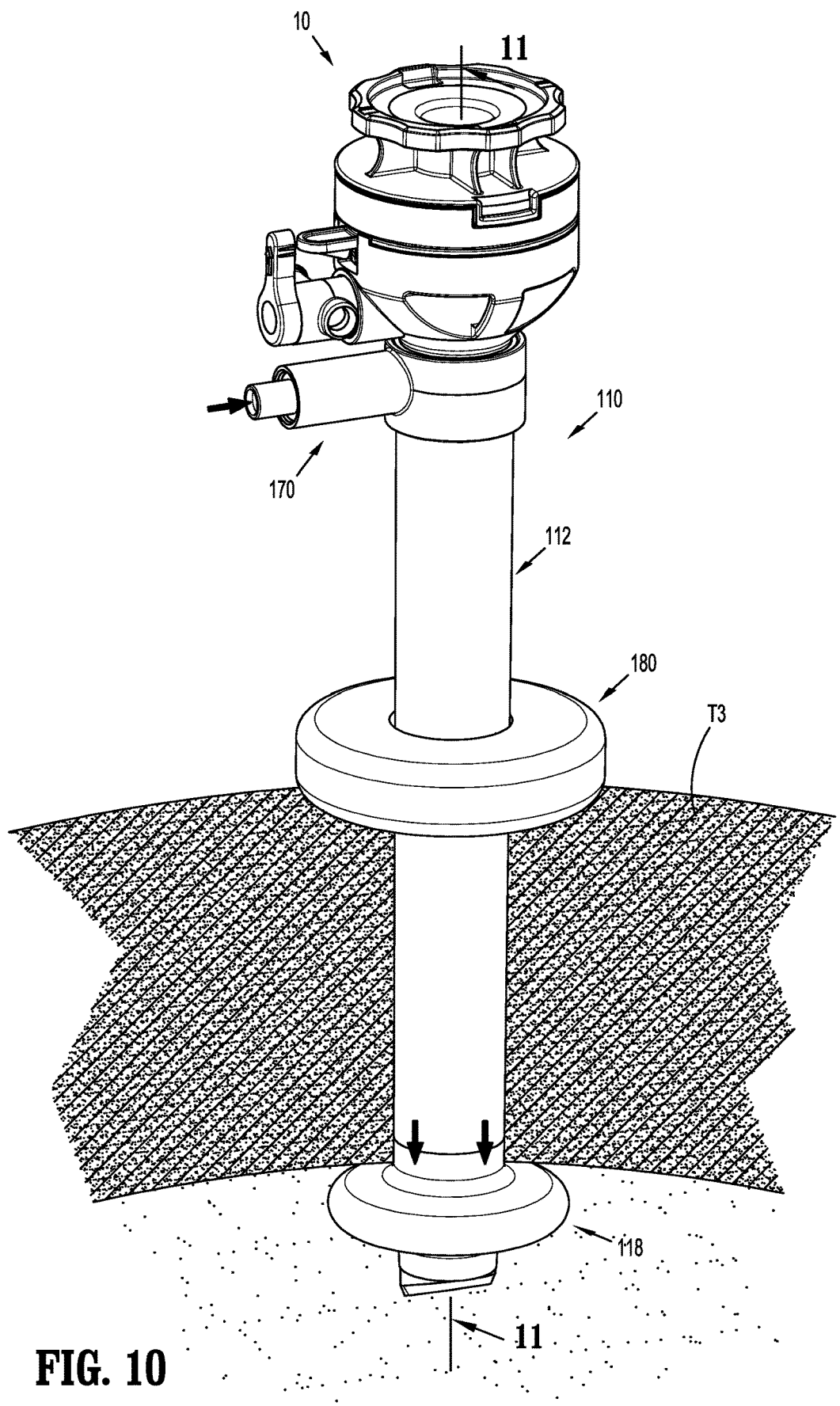
FIG. 10 is a perspective view of the surgical access assembly of FIG. 1, shown with the cannula in a fully extended position and secured to tissue.

As the proximal and distal portions 114a, 114b of the balloon 114 are secured to the shaft assembly 112 and the balloon 114 is formed from an elastic material, the shape and diameter of the balloon 114 remains relatively constant regardless of the length of the shaft assembly 112. In some aspects, the balloon 114 has a length that is the length of the shaft assembly 112 when the shaft assembly 112 is disposed in the fully extended position (FIG. 10). The sleeve 118 of the balloon 114 may fold together or bunch up when the shaft assembly 112 is in the unextended position (FIG. 6) or the semi-extended position (FIG. 7). In other aspects, the balloon 114 is formed from a highly elastic material and has a length that is less than the length of the shaft assembly 112 when the shaft assembly 112 is in the fully extended position. The balloon 114 can stretch to accommodate the shaft assembly 112 when the shaft assembly 112 is in the fully extended position.

With continued reference to FIGS. 1-3, the instrument housing 150 includes an upper housing section 152 and a lower housing section 154, and defines a cavity 151 therein that communicates with the access lumen 111 of the shaft assembly 112 of the cannula 110. The upper housing section 152 may be selectively attachable to, and detachable from, the lower housing section 154, and the lower housing section 154 may be releasably or permanently attached to the outer shaft 120 of the shaft assembly 112 of the cannula 110. In aspects, either or both of the upper and lower housing sections 152, 154 of the instrument housing 150 may include knurls, indentations, tabs, or be otherwise configured to facilitate engagement by a user.

The instrument housing 150 supports a seal assembly 156 and a valve assembly 158 therein. The seal assembly 156 is disposed proximally of the valve assembly 158. The seal assembly 156 generally includes an instrument seal 156a for sealing around surgical instruments (not shown) inserted into the cannula 110, and the valve assembly 158 generally includes a zero-closure seal 158a for sealing the access lumen 111 of the cannula 110 in the absence of a surgical instrument inserted through the cannula 110. The seal assembly 156 and the valve assembly 158 prevent the escape of the insufflation fluid therefrom, while allowing surgical instruments to be inserted therethrough and into the body cavity. The instrument seal 156a may include any known instrument seal used in cannulas and/or trocars, such as septum seal. The zero-closure seal 158a may be any known zero-closure seal for closing off the passageway into the access lumen 111, such as a duckbill seal or flapper valve.

The instrument housing 150 includes an insufflation port 160 coupled to the lower housing section 154. The insufflation port 160 defines an opening 161 therethrough that is in fluid communication with the cavity 151 of the instrument housing 150 which, in turn, is in fluid communication with the access lumen 111 of the cannula 110 to insufflate a body cavity, such as abdominal cavity (e.g., create a pneumoperitoneum). The opening 161 of the insufflation port 160 is disposed distally of the valve assembly 158 to maintain insufflation pressure within the body cavity. The insufflation port 160 is connectable to a source of insufflation fluid (not shown) for delivery of the insufflation fluid (e.g., gases) into the body cavity. The insufflation port 160 is configured and dimensioned to receive a valve 162 in a substantially fluid-tight manner. In aspects, and as shown, the valve 162 is a stopcock valve for controlling the flow of the insufflation fluid. The valve 162, however, may be any known valve for directing fluid flow and, in some aspects, regulating fluid flow.

The surgical access device 100 includes an anchor inflation port 170 coupled to the outer shaft 120 of the shaft assembly 112 of the cannula 110. The anchor inflation port 170 includes a housing 172 and a collar 174 extending from the housing 172. The collar 174 secures the housing 172 to the outer shaft 120 of the shaft assembly 112. The collar 174 extends around the outer shaft 120 and is engaged with the outer shaft 120 in a manner that fixes (e.g., longitudinally and rotationally) the anchor inflation port 170 relative to the shaft assembly 112. More particularly, the collar 174 may be engaged with the outer shaft 120 of the shaft assembly 112 by snap fit connection or in a friction fit manner. It should be understood that other mating structures and relationships may be utilized to secure the anchor inflation port 170 to the outer shaft 120 of the shaft assembly 112.

The anchor inflation port 170 is in fluid communication with the expandable anchor 118 of balloon 114. The housing 172 of the anchor inflation port 170 defines a cavity 171 therein that is in fluid communication with inflation channel 121 of the outer shaft 120 of the cannula 110 which, in turn, is in fluid communication with the expandable anchor 118 of the balloon 114. The housing 172 is connectable to a fluid source (not shown) for delivery of a fluid (e.g., gases) into the expandable anchor 118. The anchor inflation port 170 includes a valve 176 operably coupled to the housing 172 in a substantially fluid-tight manner. In aspects, and as shown, the valve 176 is a check valve that allows the fluid to flow into the expandable anchor 118 and prevents reverse flow of the fluid therefrom. The valve 176, however, may be any known valve for controlling fluid flow. In some aspects, the anchor inflation port 170 may further include a release valve (not shown) to allow the escape of fluid from the expandable anchor 118 and/or limit pressure that can build up in the expandable anchor 118.

The inflation channel 121 defined in the outer shaft 120 provides a pathway for fluid flow from the fluid source (not shown) to the expandable anchor 118. The proximal end 121a of the inflation channel 121 is disposed within the cavity 171 of the housing 172 of the anchor inflation port 170 and in fluid communication therewith to provide an inlet from the fluid source (not shown) during inflation and an outlet into the cavity 171 during deflation. The distal end 121b of the inflation channel 121 is disposed within or adjacent to the expandable anchor 118 and is in fluid communication therewith to provide an inlet into the expandable anchor 118 during inflation and an outlet from the expandable anchor 118 during deflation.

To inflate the expandable anchor 118, a fluid source (not shown) is releasably attached to the anchor inflation port 170 and pressurized fluid is introduced into the anchor inflation port 170, through the inflation channel 121, and into the expandable anchor 118 causing the expandable anchor 118 to expand. To deflate the expandable anchor 118, the valve 176 of the anchor inflation port 170 may be actuated to depressurize the fluid and allow it to escape therethrough causing the expandable anchor 118 to retract or collapse.

The retention collar 180 is supported on the shaft assembly 112 of the cannula 110. The retention collar 180 includes an annular body 182 having an opening 183 defined therethrough that is sized and shaped to accommodate the shaft assembly 112 of the cannula 110 therein. The retention collar 180 is releasably engageable with shaft assembly 112, and slidable therealong to adjust the longitudinal position of the retention collar 180 on the shaft assembly 112. The retention collar 180 is configured to frictionally engage any of the outer, intermediate, and inner shafts 120, 130, 140 of the shaft assembly 112 to limit movement of the retention collar 180 relative to the cannula 110 and to secure the cannula 110 against an outer surface of a body wall (see e.g., FIG. 6). The retention collar 180 may be formed from a compressible material (e.g., foam) to aid in sealing the opening into the tissue of the body wall. The retention collar 180 may include any known retention mechanism used on cannulas and/or trocars, such as foam collars.

Figure 4:
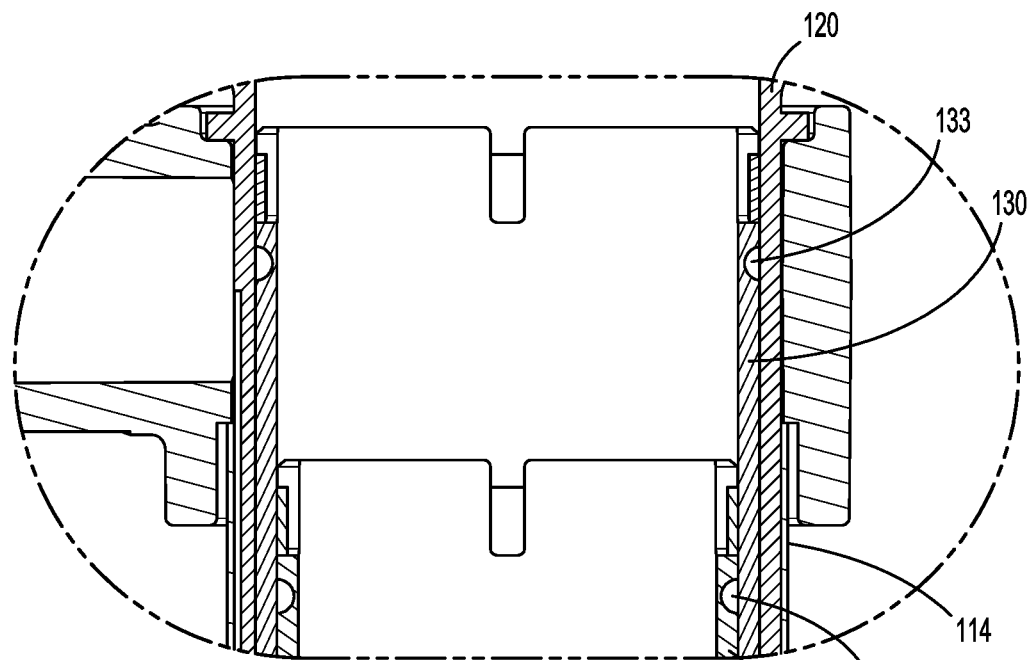
FIG. 4 is a close-up view of the area of detail indicated in FIG. 3.
Figure 5:
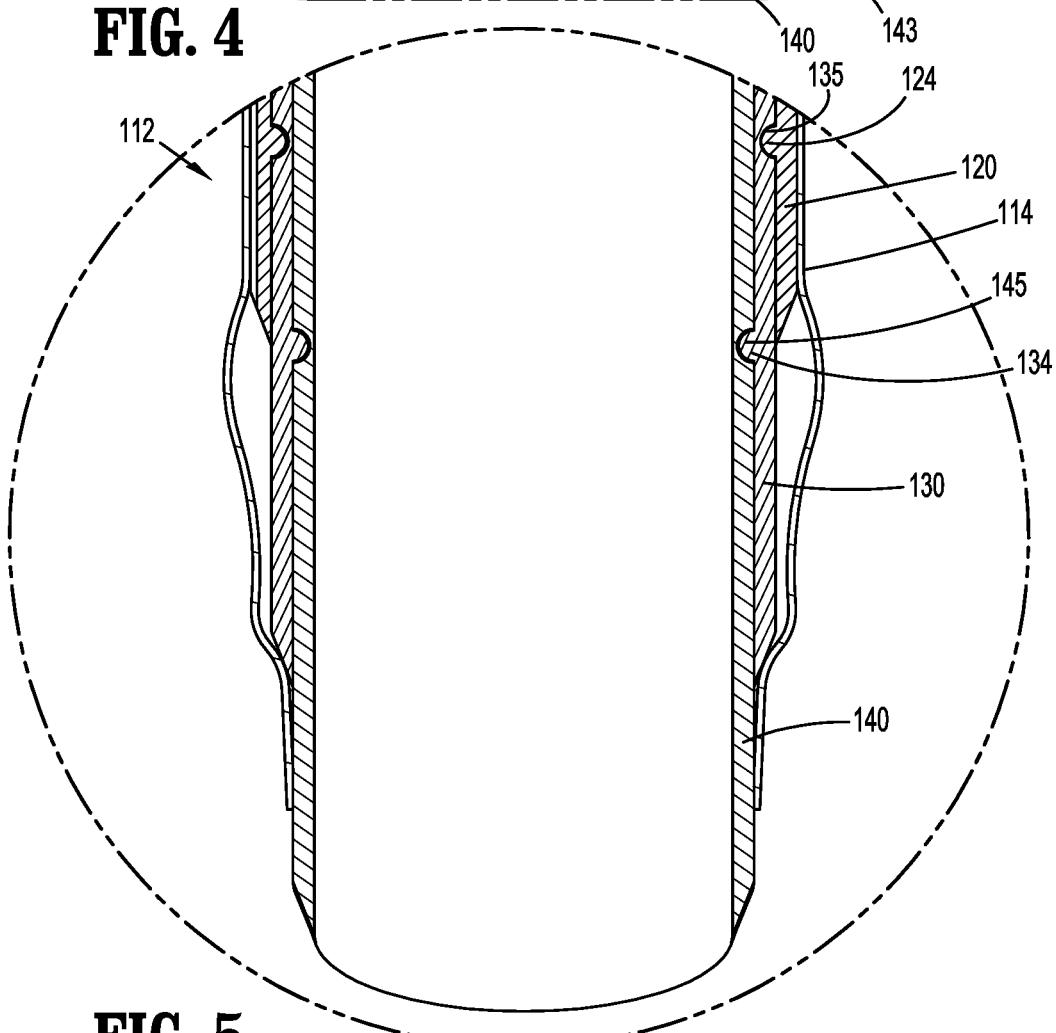
FIG. 5 is a close-up view of the area of detail indicated in FIG. 3.

Turning now to FIGS. 3-5, the surgical access assembly 10 is shown with the shaft assembly 112 of the cannula 110 in an unextended position and the balloon 114 deflated. In the unextended position, the cannula 110 is at its shortest length with the inner shaft 140 disposed within the intermediate shaft 130 in a proximal-most position and the intermediate shaft 130 disposed within the outer shaft 120 in a proximal-most position. As seen in FIG. 3, the distal end portion 130b of the intermediate shaft 130 extends distally beyond the distal end portion 120b of the outer shaft 120, and the distal end portion 140b of the inner shaft 140 extends distally beyond the distal end portion 130b of the intermediate shaft 130. As seen in FIG. 4, the proximal annular grooves 133, 143 of the intermediate and inner shafts 130, 140 are free and not engaged or mated with any structure of the outer or intermediate shafts 120, 130, respectively. As seen in FIG. 5, the distal annular grooves 135, 145 of the intermediate and inner shafts 130, 140 are engaged with the annular ridges 124, 134 of the outer and intermediate shafts 120, 130, respectively, to retain the shaft assembly 112 in the unextended position. Specifically, the distal annular groove 135 of the intermediate shaft 130 mates with the annular ridge 124 of the outer shaft 120, and the distal annular groove 145 of the inner shaft 140 mates with the annular ridge 134 of the intermediate shaft 130.

Figure 6:
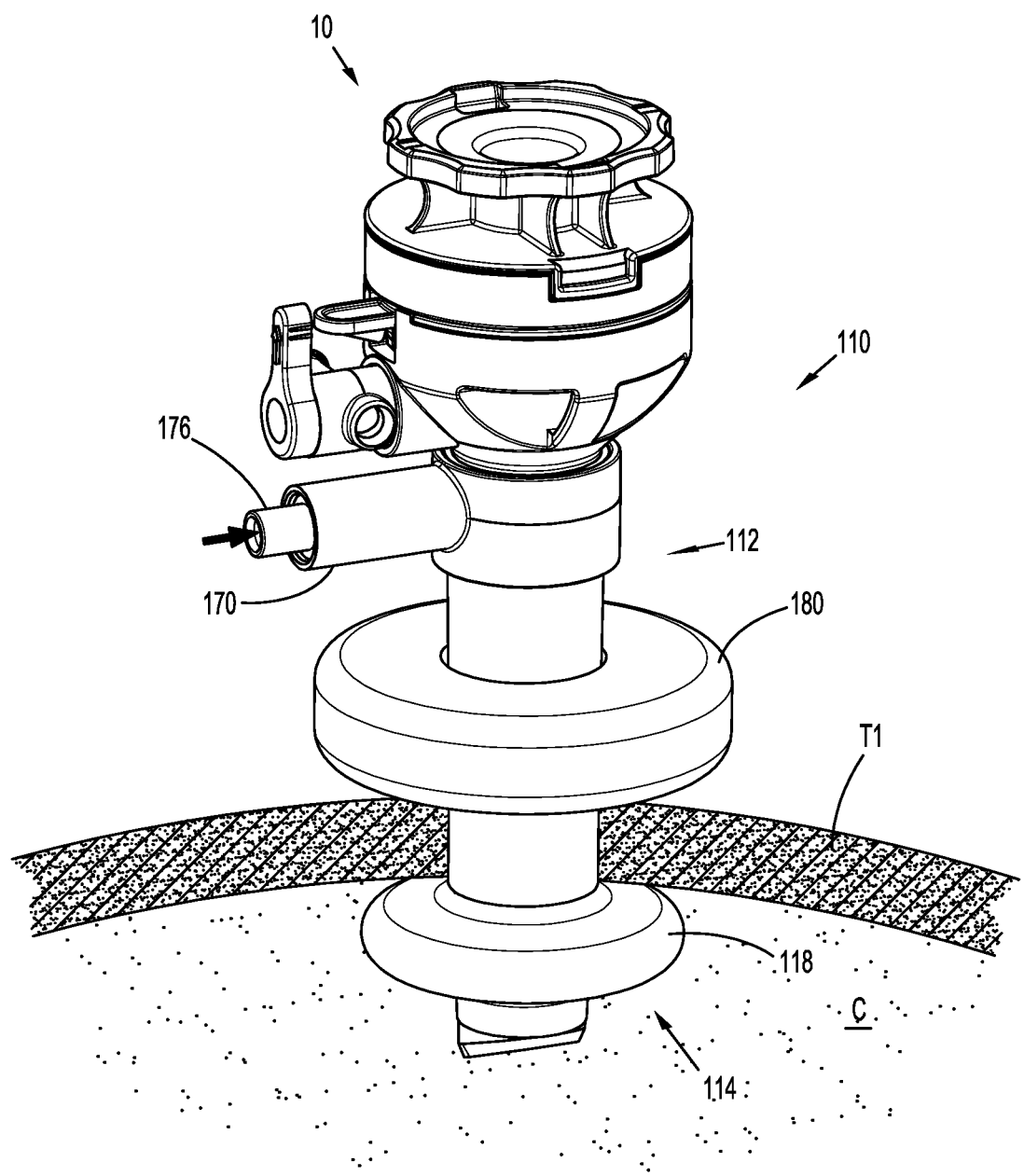
FIG. 6 is a perspective view of the surgical access assembly of FIG. 1, shown secured to tissue.
Figure 7:
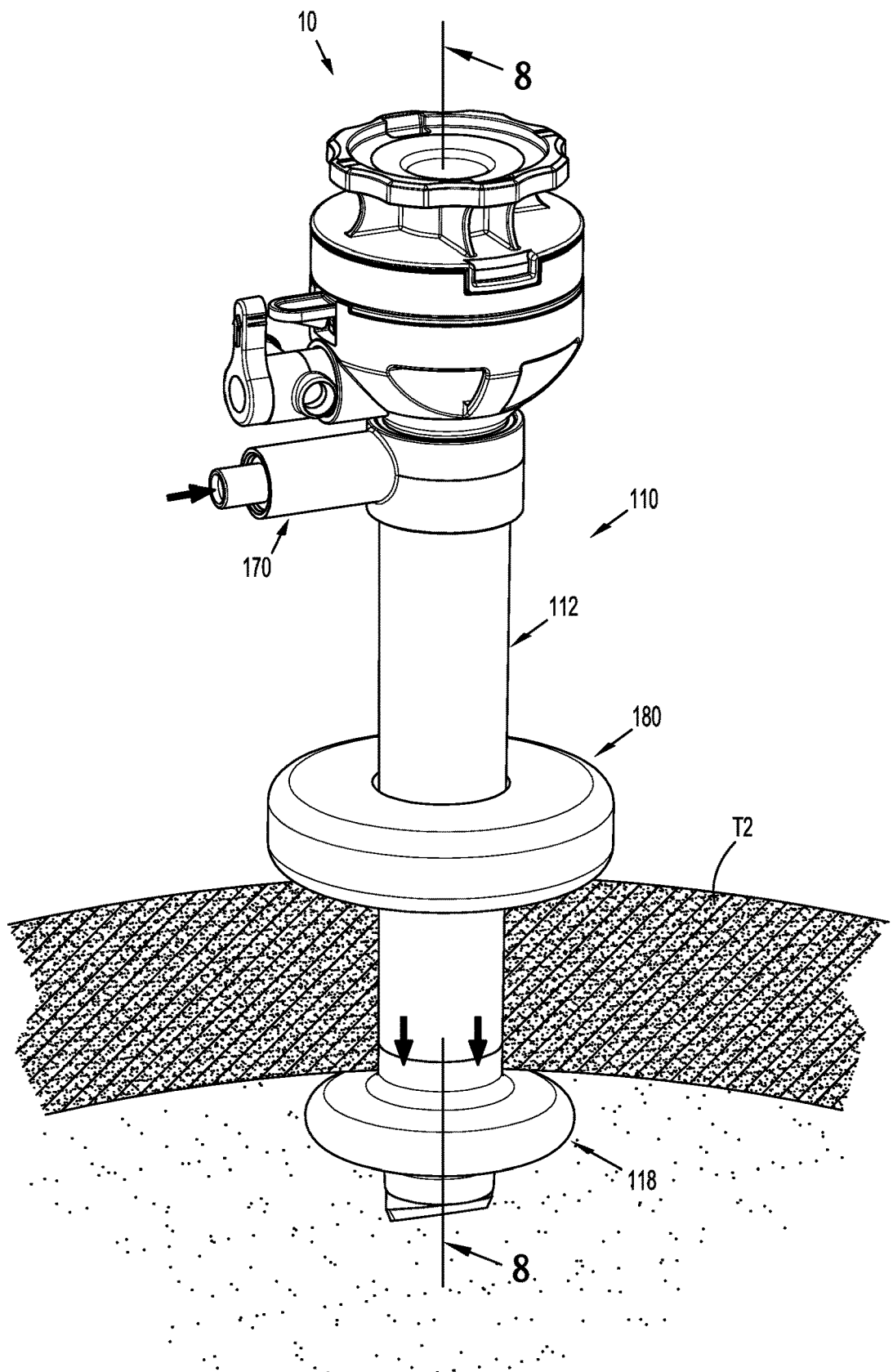
FIG. 7 is a perspective view of the surgical access assembly of FIG. 1, shown with the cannula in a partially extended position and secured to tissue.

FIG. 6 illustrates the surgical access assembly 10 disposed within tissue "T1," e.g., an abdominal wall, with the cannula 110 in the unextended position. In a method of use, the shaft assembly 112 of the cannula 110 is received through the tissue "T1" (e.g., by utilizing an obturator (not shown) to facilitate entry of the cannula 110 through the tissue "T1"), and the expandable anchor 118 of the balloon 114 is inflated within a body cavity "C" to prevent the cannula 110 from being withdrawn through the tissue "T1." The expandable anchor 118 is inflated by introducing fluid from a fluid source (not shown) into the valve 176 of the anchor inflation port 170, through the inflation channel 121 (FIG. 3), and into the expandable anchor 118. The retention collar 180 is slid distally along the shaft assembly 112 (e.g., the outer shaft 120) of the cannula 110 until the retention collar 180 abuts or presses on the tissue "T1." The tissue "T1" is thus sandwiched between the expandable anchor 118 and the retention collar 180 to prevent the cannula 110 from being withdrawn from or over-inserted into the tissue "T1." In this manner, the surgical access assembly 10 is secured to the tissue "T1" and longitudinal movement of the cannula 110 relative to the tissue "T1" is prevented or minimized throughout insertion, withdrawal, and/or manipulation of a surgical instrument (not shown) through the cannula 110. Following the surgical procedure, the expandable anchor 118 is deflated to permit the withdrawal of the surgical access assembly 10 from the tissue "T1."

Figure 8:
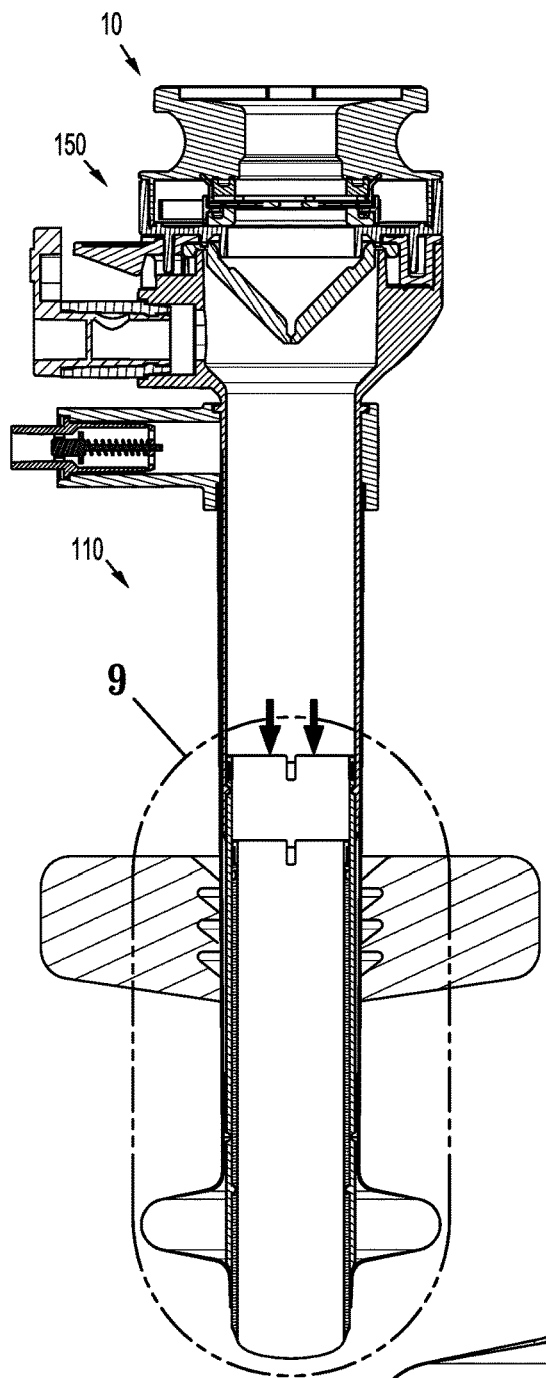
FIG. 8 is a cross-sectional view of the surgical access assembly of FIG. 7, taken along section line 8-8 of FIG. 7.
Figure 9:
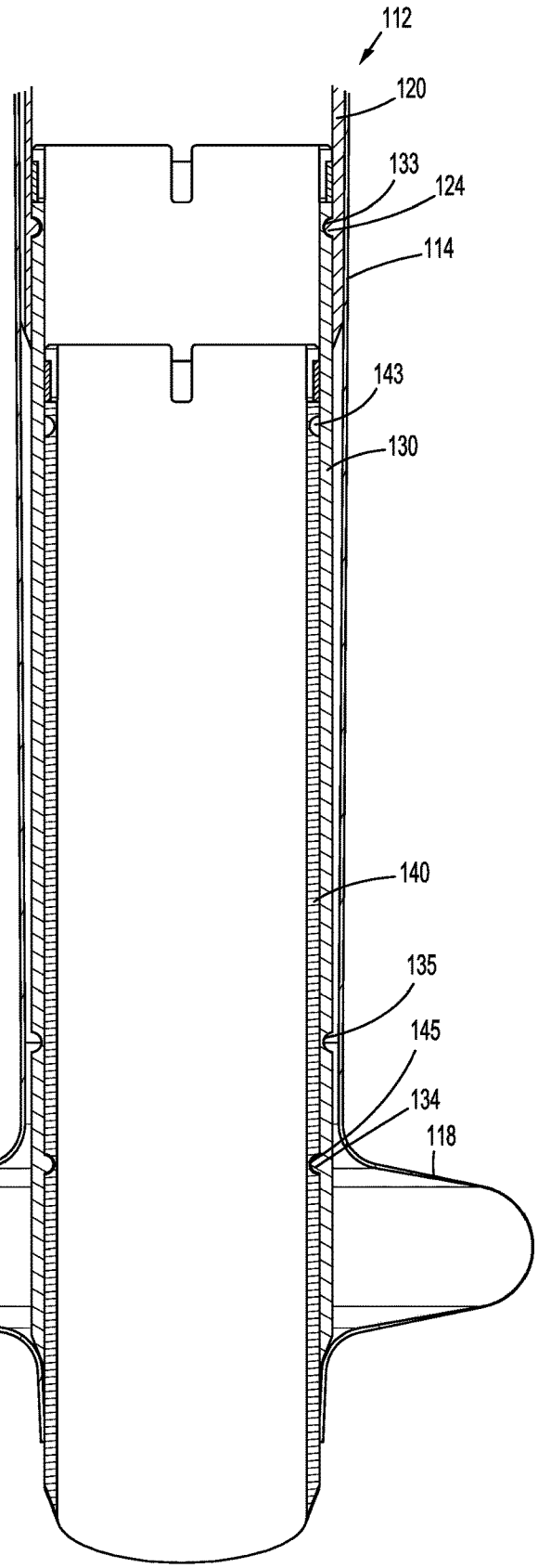
FIG. 9 is a close-up view of the area of detail indicated in FIG. 8.

As shown in FIGS. 7-9, the cannula 110 is moved to a semi-extended or partially extended position for positioning within tissue "T2" that is thicker than tissue "T1" (FIG. 6). The surgical access assembly 10 is used in the same manner as described above with regard to tissue "T1", however, the pressure of the fluid from the fluid source into the anchor inflation port 170 is increased to move the shaft assembly 112 distally from the unextended position to the semi-extended position. Alternatively, the shaft assembly 112 may be moved to the semi-extended position manually. During movement to the semi-extended position, the intermediate shaft 130 is moved distally relative to the outer shaft 120 such that the distal annular groove 135 of the intermediate shaft 130 disengages from the annular ridge 124 of the outer shaft 120 and is free. The intermediate shaft 130 slides distally until the proximal annular groove 133 engages and mates with the annular ridge 124 of the outer shaft 120. In the semi-extended position, the intermediate shaft 130 is disposed within the inner shaft 120 in a distal-most position and the inner shaft 140 remains in the same position relative to the intermediate shaft 130 as when in the unextended position (e.g., the proximal-most position) with the proximal annular groove 143 of the inner shaft 140 free from engagement and the distal annular groove 145 engaged with the annular ridge 134 of the intermediate shaft 130.

Figure 11:
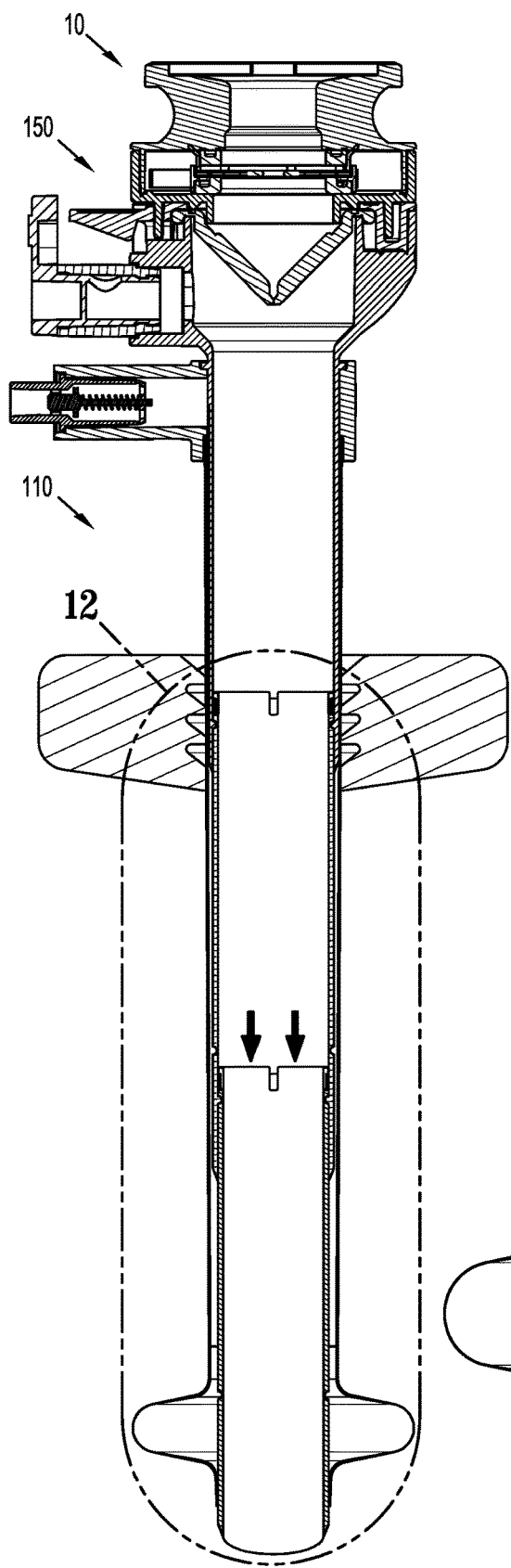
FIG. 11 is a cross-sectional view of the surgical access assembly of FIG. 10, taken along section line 11-11 of FIG. 10.
Figure 12:
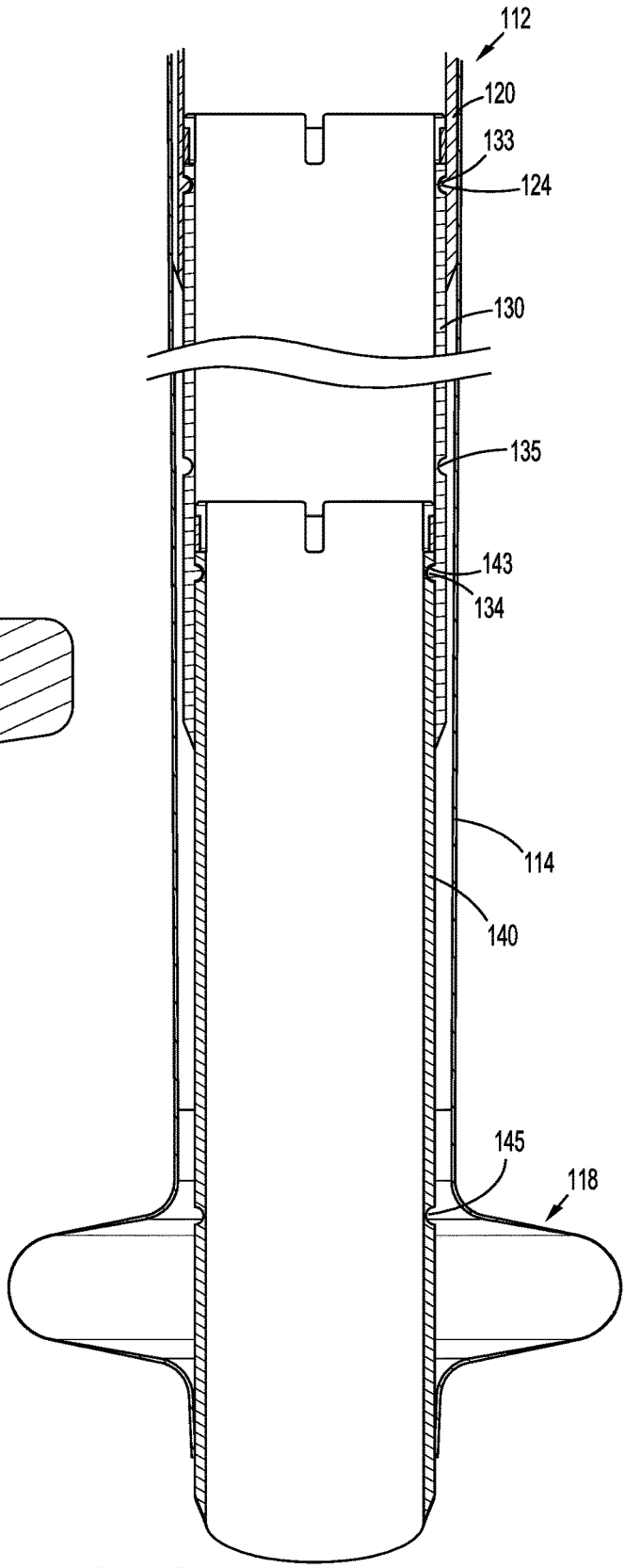
FIG. 12 is a close-up view of the area of detail indicated in FIG. 11.

As shown in FIGS. 10-12, the cannula 110 is moved to an extended or fully extended position for positioning within tissue "T3" that is thicker than tissue "T2" (FIG. 7). The surgical access assembly 10 is used in the same manner as described above with regard to tissues "T1" and "T2", however, the pressure of the fluid from the fluid source into the anchor inflation port 170 is increased to move the shaft assembly 112 distally to the fully extended position. Alternatively, the shaft assembly 112 may be moved to the fully extended position manually. During movement to the fully extended position, the inner shaft 140 is moved distally relative to the intermediate shaft 130 such that the distal annular groove 145 of the inner shaft 140 disengages the annular ridge 134 of the intermediate shaft 130 and is free. The inner shaft 140 slides distally until the proximal annular groove 143 engage and mates with the annular ridge 134 of the intermediate shaft 130. In the fully extended position, the inner shaft 140 is disposed within the intermediate shaft 130 in a distal-most position and the intermediate shaft 140 remains in the same position relative to the outer shaft 120 as when in the semi-extended position (e.g., the distal-most position) with the proximal annular groove 133 engaged with the annular ridge 124 of the outer shaft 120 and the distal annular groove 135 free from engagement.

In some aspects, the shaft assembly 112 is also movable to a plurality of partially extended positions via frictional engagement of the gaskets 138, 148 with the inner surfaces 122b, 132b of the outer and intermediate shafts 120, 130, respectively. The gasket 138 may hold the intermediate shaft 130 relative to the outer shaft 120 in a plurality of partially extended positions between the unexpanded and semi-expanded positions and the gasket 148 may hold the inner shaft 140 relative to the intermediate shaft 130 in a plurality of partially extended positions between the semi-expanded and fully expanded positions.

While the outer, intermediate, and inner shafts 120, 130, 140 are shown as being substantially circular cylinders, it should be understood that they may be any shape telescopically arranged and slidable relative to each other (e.g., elliptical cylinders). Further, while the annular ridges 124, 134, the proximal annular grooves 133, 143, and the distal annular grooves 135, 145 are shown as continuous ridges and grooves extending completely around the respective shaft segments, it should be understood that the ridges and grooves may be discontinuous (e.g., extend partially around the respective shaft segments) so long as the ridges and grooves are complementary and configured to mate with each other. Further still, while the intermediate and inner shafts 130, 140 are shown as including proximal annular grooves 133, 143 and distal annular grooves 135, 145, it should be understood that the intermediate shaft and/or the inner shaft may include additional grooves to accommodate additional lengths of the shaft assembly 112. Additionally or alternatively, while the lengths of the outer, intermediate, and inner shafts 120, 130, 140 are shown as being substantially the same, it should be understood that the lengths of the shaft segments may vary (e.g., the outer shaft may be longer than the intermediate shaft and/or the inner shaft). Moreover, while the shaft assembly 112 is shown including three shaft segments, it should be understood that the shaft assembly may include two shaft segments (e.g., an outer shaft and an inner shaft) or more than three shaft segments (e.g., an outer shaft, two or more intermediate shafts, and an inner shaft).

Referring now to FIG. 13, a surgical access device 200 in accordance with another aspect of the present disclosure is shown. The surgical access device 200 includes a cannula 210 and an instrument housing 250. The cannula 210 includes a shaft 212 extending along a longitudinal axis "X" and defining an access lumen 211 for reception and passage of a surgical instrument (not shown) therethrough. The shaft 212 includes proximal and distal end portions 212a, 212b having fixed lengths and a central portion 212c having a variable length. The central portion 212c includes a plurality of annular folds 213, in the manner of an accordion, formed therein such that the shaft 212 is movable between an unextended position to a fully extended position, as well as a multitude of partially extended positions therebetween, as described in further detail below. The shaft 212 is formed from a material that is substantially rigid so as to hold the shape of the shaft 212 yet flexible to allow for length adjustment (e.g., extension or retraction of the annular folds 213). The shaft 212 may be molded so that the shaft 212 can be extended or retracted similar to an accordion.

A proximal end portion 210a of the cannula 210 supports the instrument housing 250 thereon. Specifically, as seen in FIG. 14, the proximal end portion 210a of the cannula 210 includes a threaded inner surface 215 that is configured to mate with a threaded outer surface 255 of the instrument housing 250. However, it should be understood that other mating structures and/or attachment methods may be utilized to secure the instrument housing 250 to the cannula 210 or the instrument housing 250 and the cannula 210 may be integrally formed. The instrument housing 250 is otherwise substantially the same as instrument housing 150 (e.g., the instrument housing 250 includes upper and lower housing sections, a seal assembly, a valve assembly, and an insufflation port).

Figure 15:
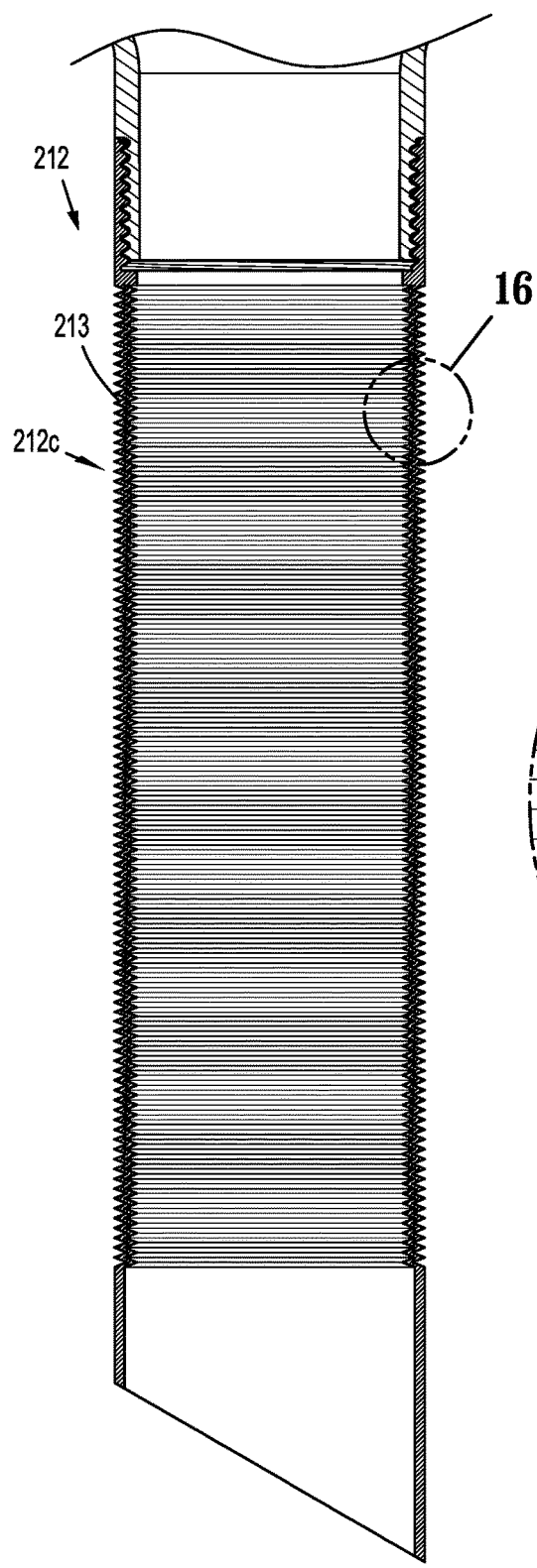
FIG. 15 is a cross-sectional view of the surgical access device of FIG. 13, taken along section line 15-15 of FIG. 13.
Figure 16:
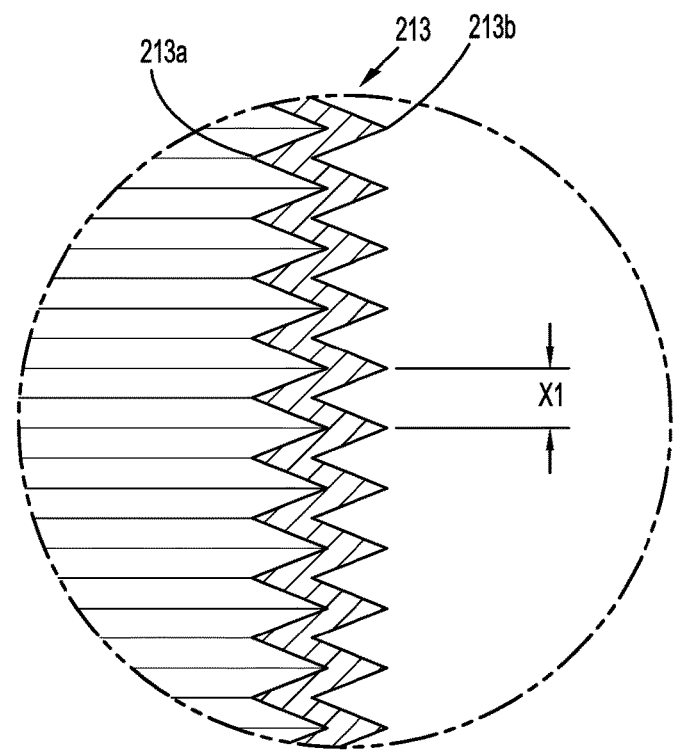
FIG. 16 is a close-up view of the area of detail indicated in FIG. 15.

As shown in FIGS. 15-18, the annular folds 213 extend circumferentially around the shaft 212 such that the central portion 212c can be longitudinally extended or retracted. The annular folds 213 are formed with oppositely directed and alternating inner and outer fold peaks 213a, 213b. The outer fold peaks 213b may be pointed (e.g., sharp or spiked) to provide grips for tissue fixation. As seen in FIGS. 15 and 16, in an unextended position, adjacent outer fold peaks 213b are spaced an axial distance "x1" relative to each other. As seen in FIGS. 17 and 18, the shaft 212 may be moved to an extended position in which the annular folds 213 move axially apart to accommodate a longer length of the central portion 212c such that adjacent outer fold peaks 213b are spaced an axial distance "x2" relative to each other. The axial distance "x2" is greater than the axial distance "x1" (FIG. 16). Accordingly, the central portion 212c of the elongated body 212 may be retracted by axially pushing the annular folds 213 closer together (e.g., in an overlapping configuration) to create the shortest possible length of the shaft 212 and expanded by axially pulling the annular folds 213 apart to create a longer length. The length of the shaft 212 may be selected to accommodate the thickness of a tissue wall.

In a method of use, the shaft 212 of the cannula 210 is inserted into tissue in a fully extended position so that an obturator (not shown) can be used without needing to accommodate multiple length cannulas. Once inserted into the tissue, the shaft 212 can be retracted to set the optimal length of the cannula 210 for the tissue wall.

While the cannula 210 is shown including the annular folds 213 along a majority of the length of the shaft 212, it should be understood that the annular folds 213 may be provided in a portion of the length of the elongated shaft. For example, the annular folds 213 may be provided in a distal half of the shaft 212 and a retention collar 180 (FIG. 1) may be utilized with the surgical access device 200 for added fixation. Further, the surgical access device 200 may include a balloon for advanced fixation. For example, the surgical access device 200 may include an anchor inflation port 170 (FIG. 1) coupled to the proximal end portion 212a of the shaft 212 and an expandable anchor 118 (FIG. 1) coupled to the distal end portion 212b of the shaft 212, and an inflation lumen (not shown) extending between the anchor inflation port and the expandable anchor (e.g., a tube extending through the access lumen of the cannula).

While aspects of the disclosure have been described and shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:
1. A surgical access device comprising:
a cannula including a shaft assembly, the shaft assembly including:
an outer shaft;
an intermediate shaft disposed within and longitudinally slidable relative to the outer shaft; and
an inner shaft disposed within and longitudinally slidable relative to the intermediate shaft,
the shaft assembly movable between an unextended position, a fully extended position, and a semi-extended position between the unextended position and the fully extended position; and a balloon operably associated with the cannula, the balloon including a proximal portion secured to the outer shaft of the shaft assembly and a distal portion secured to the inner shaft of the shaft assembly.

2. The surgical access device according to claim 1, wherein the inner shaft is movable within the intermediate shaft between a proximal-most position and a distal-most position and the intermediate shaft is movable within the outer shaft between a proximal-most position and a distal-most position and wherein, when the shaft assembly is in the unextended position, the inner and intermediate shafts are in the proximal-most positions and when the shaft assembly is in the fully extended position, the inner and intermediate shafts are in the distal-most positions.

3. The surgical access device according to claim 2, wherein, when the shaft assembly is in the semi-extended position, the inner shaft is in the proximal-most position and the intermediate shaft is in the distal-most position.

4. The surgical access device according to claim 1, wherein a distal end portion of the outer shaft includes an annular ridge on an inner surface of the outer shaft, and the intermediate shaft includes a proximal annular groove and a distal annular groove defined in an outer surface of the intermediate shaft, and wherein, when the shaft assembly is in the unextended position, the annular ridge of the outer shaft is engaged with the distal annular groove of the intermediate shaft and, when the shaft assembly is in the semi-extended and fully extended positions, the annular ridge of the outer shaft is engaged with the proximal annular groove of the intermediate shaft.

5. The surgical access device according to claim 1, wherein a distal end portion of the intermediate shaft includes an annular ridge on an inner surface of the intermediate shaft, and the inner shaft includes a proximal annular groove and a distal annular groove defined in an outer surface of the inner shaft, and wherein, when the shaft assembly is in the unextended and semi-extended positions, the annular ridge of the intermediate shaft is engaged with the distal annular groove of the inner shaft and, when the shaft assembly is in the fully extended position, the annular ridge of the intermediate shaft is engaged with the proximal annular groove of the inner shaft.

6. The surgical access device according to claim 1, further including a first gasket disposed between the intermediate and outer shafts and a second gasket disposed between the inner and intermediate shafts.

7. The surgical access device according to claim 6, wherein an annular recess is defined in an outer surface of the intermediate shaft and an annular recess is defined in an outer surface of the inner shaft, and the first gasket is received within the annular recess of the intermediate shaft and the second gasket is received within the annular recess of the inner shaft.

8. The surgical access device according to claim 1, wherein an inflation channel is defined in an outer surface of the outer shaft of the shaft assembly, and the inflation channel is in fluid communication with the balloon.

9. The surgical access device according to claim 8, further including an anchor inflation port coupled to the outer shaft of the shaft assembly and in fluid communication with the inflation channel of the outer shaft.

10. The surgical access device according to claim 9, wherein a proximal end of the inflation channel is disposed within the anchor inflation port and a distal end of the inflation channel is disposed within the balloon.

11. The surgical access device according to claim 1, further including an instrument housing coupled to the cannula.

12. The surgical access device according to claim 11, wherein the instrument housing is secured to the outer shaft of the shaft assembly of the cannula.

13. The surgical access device according to claim 1, further including a retention collar movably positioned along the shaft assembly of the cannula.

14. The surgical access device according to claim 1, wherein a proximal end portion of the intermediate shaft includes a proximally extending collar having a first collar section and a second collar section that are configured to flex during movement of the intermediate shaft relative to the outer shaft, and a proximal end portion of the inner shaft includes a proximally extending collar having a first collar section and second collar section that are configured to flex during movement of the inner shaft relative to the intermediate shaft.

15. The surgical access device according to claim 1, wherein the proximal portion of the balloon is secured to a proximal end portion of the outer shaft and the distal portion of the balloon is secured to a distal end portion of the inner shaft.

16. The surgical access device according to claim 1, wherein the balloon includes a sleeve and an expandable anchor.

17. The surgical access device according to claim 1, wherein the balloon is formed from an elastic material.

18. The surgical access device according to claim 1, wherein the balloon has a length that is the same as a length of the shaft assembly when the shaft assembly is disposed in the fully extended position.

19. The surgical access device according to claim 1, wherein the balloon has a length that is less than a length of the shaft assembly when the shaft assembly is disposed in the fully extended position.

20. A surgical access device comprising:
a cannula including a shaft assembly, the shaft assembly including at least three shaft segments telescopically mated and longitudinally slidable relative to each other, the shaft assembly movable between an unextended position, a fully extended position, and at least one semi-extended position that is between the unextended position and the fully extended position; and
a balloon operably associated with the cannula, the balloon including a proximal portion secured to an outermost shaft segment of the at least three shaft segments and a distal portion secured to an innermost shaft segment of the at least three shaft segments.

* * * * *